(12) United States Patent
Wien

(10) Patent No.: US 8,246,647 B2
(45) Date of Patent: Aug. 21, 2012

(54) NOSTRIL DILATOR

(75) Inventor: Abraham Wien, Boca Raton, FL (US)

(73) Assignee: Abraham Wien, Boca Raton, FL (US)

( * ) Notice: Subject to any disclaimer, the term of this patent is extended or adjusted under 35 U.S.C. 154(b) by 796 days.

(21) Appl. No.: 12/291,987

(22) Filed: Nov. 14, 2008

(65) Prior Publication Data

US 2010/0125295 A1    May 20, 2010

(51) Int. Cl.
*A61M 29/00* (2006.01)

(52) U.S. Cl. ....................................................... 606/199

(58) Field of Classification Search .................. 606/199, 606/191, 196, 204.45; 128/200.24, 204.12, 128/206.11, 206.18; 623/10, 66.1
See application file for complete search history.

(56) References Cited

U.S. PATENT DOCUMENTS

| | | | |
|---|---|---|---|
| 576,441 A | 2/1897 | Farmer | |
| 1,014,076 A | 1/1912 | McConnell | |
| 1,069,459 A | 8/1913 | Myles | |
| 1,077,574 A | 11/1913 | Woodward | |
| 1,481,581 A * | 1/1924 | Woodward | 606/199 |
| 1,743,993 A | 1/1930 | Washington | |
| 2,010,485 A | 8/1935 | Heath | |
| 3,935,859 A | 2/1976 | Doyle | |
| 4,201,217 A | 5/1980 | Slater | |
| 5,706,800 A | 1/1998 | Cronk et al. | |
| 5,769,089 A | 6/1998 | Hand et al. | |
| 5,931,852 A * | 8/1999 | Brennan | 606/199 |
| 5,931,854 A | 8/1999 | Dillon | |
| 6,093,169 A | 7/2000 | Cardoso | |
| 6,238,411 B1 | 5/2001 | Thorner | |
| 6,386,197 B1 * | 5/2002 | Miller | 128/206.11 |
| 6,631,714 B2 | 10/2003 | Duyke et al. | |
| 2003/0195552 A1 * | 10/2003 | Santin | 606/199 |

* cited by examiner

*Primary Examiner* — Gary Jackson
*Assistant Examiner* — Lindsey Bachman

(57) ABSTRACT

An internal nasal prosthesis of unitary construction. The prosthesis has three distinct segments, an arched medial segment and two lateral appendages on each end of the medial segment. Each appendage of this prosthesis is the mirror image of the other and is inclined at a compound angle, relative to said arched medial segment, so that each of said appendage is inclined, at an angle, into the plane of the page, of at least about 30 degrees, and at an angle, relative to the horizontal plane of the medial section, of about 90 degrees.

7 Claims, 3 Drawing Sheets

NOSTRIL DILATOR

BACKGROUND OF THE INVENTION

1. Field of the Invention

This invention relates to a device. More specifically, this invention is directed to a device for relieving congestion and improve air flow in restricted nasal passages, by the dilation thereof with an internal prosthesis placed within the nasal passages of an individual. This prosthesis is adjustable, and under tension, so as to thereby exert constant pressure within each nasal passage to maintain such passages in a relatively dilated/open position.

2. Description of the Prior Art

The natural tendency is for human beings to breath through their nose, unless otherwise restricted from doing so. When such restriction is encountered, for any one of number of reasons, breathing is shifted to the mouth, which in turn can result in snoring, and possibly other conditions associated therewith (e.g. restrictive apnea).

Over the years a number of devices have been developed to lessen the nasal restriction and improve nasal breathing patterns. These devices fall into two broad categories: internal prosthesis and external prosthesis.

The more widely accepted of these devices, an external prosthesis, comprises a spring-like element that has an adhesive coating on one surface thereof. U.S. Pat. No. 5,769,089 (Hand et al., issued Jun. 23, 1998) is representative of this category of device. In brief, the Hand device comprises an external "nasal splint" of composite construction (3 layers). The Hand device includes a planar sheet, a strip of high density polyethylene and an adhesive layer. In practice, the Hand device is placed, in a conforming relation, on surface of the nose, with the adhesive layer proximate to, and in an adherent contact relationship with the skin. Upon placement and adherence of the Hand device on the nose, the high flexural modulus of the plastic strip recoils, and pulls the nostrils of the wearer outward while the external nasal splint is worn. By pulling the nostrils outward, the external nasal splint reportedly opens the nasal passage, thereby improving breathing and alleviating problems such as snoring.

The internal nasal prosthesis are represented by U.S. Pat. No. 6,386,197 (to Miller, issued May 14, 2002); U.S. Pat. No. 4,201,217 (to Thorner, issued May 29, 2001); and U.S. Pat. No. 6,238,411 (to Slater, issued May 8, 1980).

The Miller device includes a pair of conical shaped tubular element that is placed within each nostril. These tubular elements have what can best be described a radial array of "hose barbs" to prevent their being dislodged during use. Presumably the main advantage of the Miller design is aesthetic—the tubular elements are not visible during use.

The Thorner prosthetic device comprises an "internal nasal dilator" of composite construction. More specifically, the Thorner internal dilator is the product of a combination of several elements; specifically a V-shaped member, such as a flat spring is provided, with resilient pad means attached at each end thereof. The V-shaped member or the flexible nasal strip is then attached to the nose by the wearer at the central portion (outside bottom), by means of an adhesive element which extends from or near the free unattached ends of strip. The V-shaped spring element of the device, with the pad means, is inserted into each nostrils of the wearer, so the spring can spread the outer walls of the nose, and thereby increase the nasal opening for improved breathing. The adhesive portions at the free strip-ends are pressed against the outer surfaces of the nose by the wearer for retaining the pad means in place, inside the nose. The bias on the spring element is pre-set and does not appear to adjustable to accommodate different sized nostril openings.

The Slater prosthetic device comprises a "nasal dilator" in the form of "U" shaped bow. The "U" shaped bow has two "legs", one of which is placed in each nostril. Because of the tension on the bow, and the outward pressure exerted by each leg of the bow on each nostril, the nostrils are dilated. In order to maintain the requisite degree of tension/pressure on each nostril by the bow, an "expander" or "bridge" is placed between each leg of the bow to insure a contact spacing (spreading) of the legs of the bow. The "expander" or "bridge" is manually adjusted, to lock the legs of the bow in a pre-set configuration, prior to the insertion of the bow into the nostrils.

As is evident from the foregoing, neither of the design configurations of the presently available internal or external prosthetic devices for relieving nasal restriction, are without their shortcomings. More specifically, the external devices, of the type illustrated by the Hand patent, are limited in the amount of expansive pressure that can be exerted upon each nostril by the adhesive forces that can be applied to the external surface of the nose. Similarly, the internal devices of the type illustrated by the Thorner and Slater patents lack the ability to apply a constant pressure from with each nostril without periodic manual adjustment and the repositioning such device on a periodic basis. Accordingly, while the external device prosthetic device of Hand is favored because of the constant pressure, spring tensioning element incorporated therein, it lacks the ability for user modulation; and, is otherwise dependent upon adhesives for its contact with the nasal passages. Accordingly, there continues to exist a need for improvement of the nasal prosthesis for relief of nasal congestion. Ideally such improvement should incorporate the advantages of the external "nasal splint" of Hand, and the internal nostril expander of Slater.

OBJECTS OF THE INVENTION

It is the object of this invention to remedy the above as well as related deficiencies in the prior art.

More specifically, it is the principle object of this invention to provide an internal nasal prosthesis for placement within the nostrils of an individual to enhance breathing through the nose.

It is yet another object of this invention, to provide an internal nasal prosthesis, of unitary construction, for placement within the nostrils of an individual to enhance breathing through the nose, by application of a uniform, symmetric and constant pressure within each nostril, so as to maintain each nostril in a relative open position without obstructing the airflow.

Additional objects of this invention include a method for the treatment of nasal congestion and related breathing disorders with a mechanical prosthesis.

SUMMARY OF THE INVENTION

The above and related objects are achieved by providing an internal nasal prosthesis wherein such prosthesis has three define segments integrated within a unitary structure. In the preferred embodiments of this invention, the prosthesis comprises a unitary body of a spring-like ribbon material having a medial segment and an appendage on each end thereof for engaging each of the nostrils of an individual. Each appendage on each end of the unitary body is preferably covered with a cotton, cellulosic or foam-like sheath to increase user comfort and absorb moisture within the user's nostrils. In one of the preferred embodiments of the engine, sheath can include a medicant, such as a decongestant, which is deliverable to the user of the prosthesis.

The unitary body is bent on each end thereof to form the appendages. The bend on each end of the unitary body forms an appendage that is the mirror image of the other. More specifically, the unitary body is twisted in a counter-clockwise direction on one end of the body; and, the other end of the unitary body is twisted in a counter clockwise direction. The amount of twist or deformation of the unitary body on each end thereof is sufficient to incline each appendage, relative to the medial section thereof, at a compound angle, so that appendage is inclined, at an angle, into the plane of the page of at least about 30 degrees, and at an angle relative to the horizontal plane of the medial section, of approximately 90 degrees. The prosthesis can thereafter be configured by the user immediately prior to use by modification of the medial section thereof. More specifically, once the appendages of the prosthesis have been formed, as above described, the medial section between the two appendages can also slightly and permanently deformed by creating an arching bow between the two ends of the unitary structure. This arching of the medial section of the prosthesis displaces the appendages on either end thereof laterally, so as laterally position each appendage at a greater distance away from the other. Thus, the angle of these appendages, relative to the horizontal plane of the prosthesis, is inclined from it original vertical position, to an angle of about forty-five degrees from the horizontal.

The prosthesis can then be positioned inside an individual's nostrils by first deflection of the arch of the medial segment so as to temporarily, internally stress the prosthesis. This deflection of the arch of the media section produces the transient effect of causing each of the appendages to once again move toward one another, thus, facilitating the placement of each appendage within a nostril of an individual. Once positioned within each nostril of the individual, the deflection of the medial segment is released, and the internal stresses upon the prosthesis are uniformly distributed throughout the prosthesis. In this more relaxed/less stressed position, the forces/tension within this unitary structure of the prosthesis is equalized throughout the entire body of the prosthesis, including the lateral appendages. More specifically, the lateral appendages on each end of the prosthesis are sprung outward so as to apply a gentile, symmetric, uniformly force which vectors on the appendages so as to deflect the nostrils to a more open position. The internal tension on the medial section of the prosthesis also results in a deflection/tortional rotation of the medial section downward and at an angle that causes it to align flush with the skin right under the nose, so as to avoid any obstruction of the air passages into the nose.

Once the prosthesis is inserted into the user's nostrils, the recoil of the medial section, causes the appendage on each end thereof, applies a gentle and constant pressure on each of the nostrils, thereby opening the airway into nostrils and relieving the physical constriction of the airway. The internal nasal prosthesis of this invention, thus, can increase nasal breathing efficiency and thereby minimize snoring.

DESCRIPTION OF THE INVENTION INCLUDING PREFERRED EMBODIMENTS

Figure 1A:
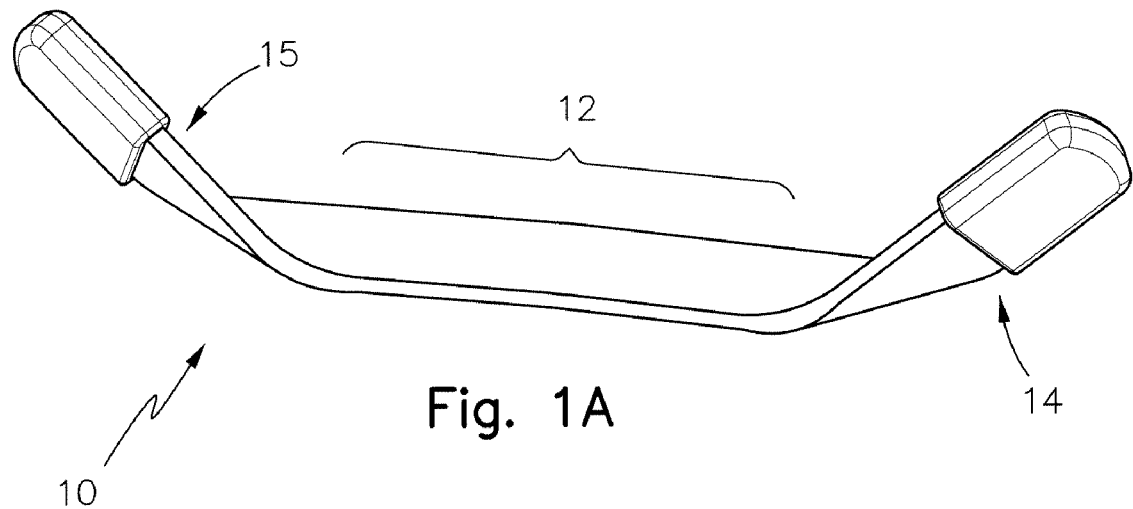
FIG. 1a depicts a perspective view of an internal nasal prosthesis of this invention prior to the imposition of internal stress to the medial segment thereof.

The reference numerals assigned to the various elements of the internal nasal prosthesis of this invention have the same numerical value where the elements in each Figure is the same or perform a function in common.

Figure 1B:
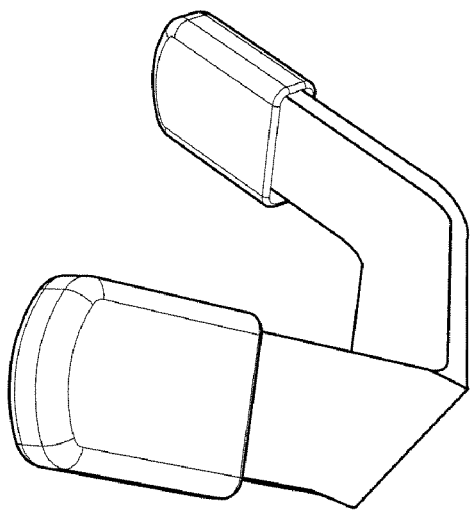
FIG. 1b depicts a perspective view of an internal nasal prosthesis of FIG. 1 when viewed for the left.
Figure 1C:
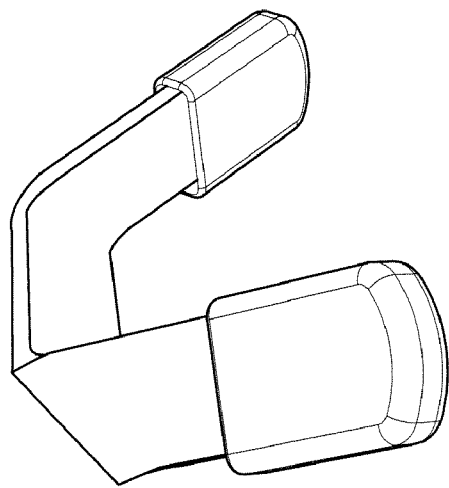
FIG. 1c depicts a perspective view of an internal nasal prosthesis of FIG. 1 when viewed for the right.

FIG. 1(a) depicts a preferred embodiment of the nasal prosthesis (10) of this invention having a medial segment (12) and two appendages (14, 15) on each end thereof. Each appendage (14, 15) is the formed so as to comprise the mirror image of the other. In the embodiment of the invention depicted in FIG. 1, the medial segment (12) is flat ribbon between each appendage (14, 15). As depicted in FIG. 1a, the appendages (14, 15) are inclined at an angle of at least about 30 degrees into the plane of the page, and at about 90 degrees from the horizontal. The relative orientation of each appendage to the medial segments is more fully appreciated when the prosthesis is view from the left end thereof (FIG. 1b) and from the right end thereof (FIG. 1c).

Figure 2:
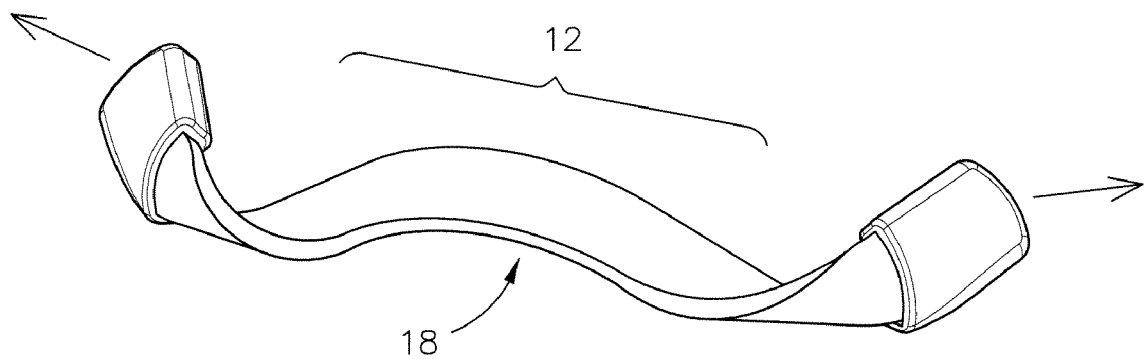
FIG. 2 depicts a perspective view of an internal nasal prosthesis of this invention subsequent to the imposition of internal stress to the medial segment thereof.

FIG. 2 depicts the nasal prosthesis of FIG. 1, that has been essentially permanently deformed by bending the medial segment to form an arch (18). The length of this medial section is different for each class of user. More specifically, if the distance between an individual's nostrils is relative small, the length of this medial section is shorter, and, conversely, if such distance is longer, the medial section will be correspondingly longer. Accordingly, the nasal prosthesis shall be made in different sizes depending upon the size/shape of an individual's head/nose, and the relative spacing ("d") between his nostrils. Ideally, a properly sized prosthesis will be deflected approximately the same for each individual, so that upon placement thereof, and release within the nostrils, the amount for tension exerted upon the lateral appendages will be about the same, and thus the comfort level and performance remain uniform from one individual to another.

Figure 3:
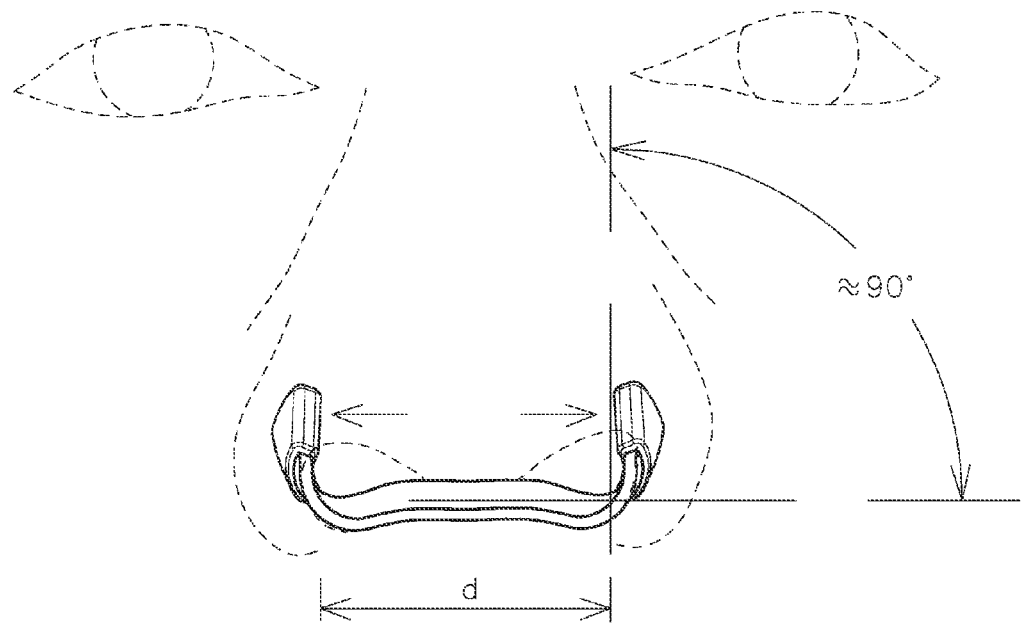
FIG. 3 depicts a perspective view of an internal nasal prosthesis of FIG. 2 when inserted into the nostrils of an individual.
Figure 4:
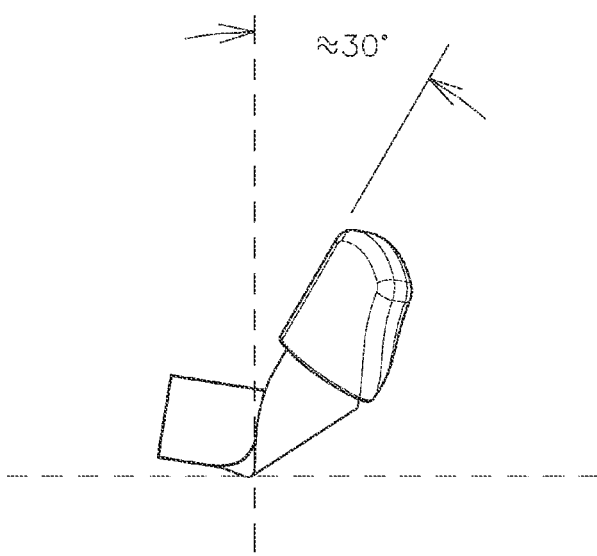
FIG. 4 is a modified side view of the internal nasal prosthesis of FIG. 3.

FIG. 3 illustrates the internal nasal prosthesis (10) in the nostrils of an individual. As shown in FIG. 3, each of the appendages (14, 15) is exerting an outward (lateral) force, in the direction indicated by the arrows, from within each nostril, to effect an expansion of the opening of each nostril. Moreover, the tension within the prosthesis results in a tortional force that causes the prosthesis to move downward, and out of the air passage in front of each nostril. As can be seen in FIGS. 3 and 4, the amount of twist or deformation of the unitary body on each end thereof is sufficient to incline each appendage, relative to the medial section thereof, for insertion into the nostrils of the wearer. The medial section may be considered to exist generally in a plane, and the appendages may be inclined, at an angle, of about 30 degrees relative to a plane that is orthogonal to the plane of the medial section and which intersects the two appendages as illustrated in FIG. 4, and at an angle relative to the horizontal plane of the medial section, of approximately 90 degrees as illustrated in FIG. 3.

The basic configuration of the prosthesis of this invention can be further modified by addition or alteration of one of more of its basic components (e.g. use or provision of replaceable pad for such appendages), without departure from the scope of the invention, which is defined in the following set of claims.

What is claimed is:

1. An internal nasal prosthesis consisting of:
   a spring-like, resilient ribbon material having
      a substantially planar medial segment existing in a first plane; and
      an appendage on each end of the medial segment for internally engaging each of the spaced apart nostrils of a user, wherein each appendage is a mirror image of the other appendage; and
   wherein each appendage is twisted at an inclined compound angle so that each appendage extends at about 30 degrees relative to a plane orthogonal to the first plane and at about 90 degrees relative to the first plane when the nasal prosthesis is worn by the user; and
   wherein when the prosthesis is worn by the user, the medial segment fits under the septum without pinching the sides of the septum.

2. The internal nasal prosthesis of claim 1, wherein the appendages are at least partially covered with a sheath.

3. The internal nasal prosthesis of claim 2, wherein the sheath is an open cell foam material.

4. The internal nasal prosthesis of claim 2, wherein the sheath is a hypoallergenic material.

5. The internal nasal prosthesis of claim 2, wherein the sheath includes a medicant.

6. The internal nasal prosthesis of claim 2, wherein the sheath includes a decongestant.

7. The internal nasal prosthesis of claim 1, wherein the medial segment has a length which is sized to permit the appendages to be inserted into the nostrils of the individual.

* * * * *